(12) United States Patent
Macikenas et al.

(10) Patent No.: US 7,060,856 B2
(45) Date of Patent: Jun. 13, 2006

(54) POLYMORPHIC FORM OF N-[(R)-2,3-DIHYDROXY-PROPOXY]-3,4-DIFLUORO-2-(2-FLUORO-4-IODOPHENYLAMINO)-BENZAMIDE

(75) Inventors: Dainius Macikenas, Livonia, MI (US); Thomas Nanninga, Kalamazoo, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/969,681

(22) Filed: Oct. 20, 2004

(65) Prior Publication Data

US 2005/0085550 A1  Apr. 21, 2005

Related U.S. Application Data

(60) Provisional application No. 60/512,980, filed on Oct. 21, 2003.

(51) Int. Cl.
*C07C 233/65* (2006.01)
*A61K 31/165* (2006.01)

(52) U.S. Cl. ..................... 564/163; 514/619
(58) Field of Classification Search ............... 564/153, 564/163; 514/619
See application file for complete search history.

(56) References Cited

U.S. PATENT DOCUMENTS

| 5,155,110 | A | 10/1992 | Connor et al. |
| 5,962,265 | A | 10/1999 | Norris et al. |
| 6,469,004 | B1 | 10/2002 | Barrett et al. |
| 2003/0060469 | A1 | 3/2003 | Ludwig et al. |
| 2004/0054172 | A1 * | 3/2004 | Barrett et al. ............ 544/59 |
| 2004/0147478 | A1 * | 7/2004 | Merriman ................ 514/46 |

FOREIGN PATENT DOCUMENTS

| EP | 0316630 | 5/1989 |
| EP | 1 262 176 | 12/2002 |
| JP | 2001/55376 | 2/2001 |
| WO | WO98/37881 | 9/1998 |
| WO | WO99/01421 | 1/1999 |
| WO | WO99/01426 | 1/1999 |
| WO | WO99/34792 | 7/1999 |
| WO | WO00/34228 | 6/2000 |
| WO | WO00/35435 | 6/2000 |
| WO | WO00/35436 | 6/2000 |
| WO | WO00/37141 | 6/2000 |
| WO | WO00/40235 | 7/2000 |
| WO | WO00/40237 | 7/2000 |
| WO | WO00/41505 | 7/2000 |
| WO | WO00/41994 | 7/2000 |
| WO | WO00/42002 | 7/2000 |
| WO | WO00/42003 | 7/2000 |
| WO | WO00/42029 | 7/2000 |
| WO | WO01/05391 | 1/2001 |
| WO | WO01/05392 | 1/2001 |
| WO | WO01/05393 | 1/2001 |
| WO | WO01/47897 | 7/2001 |
| WO | WO01/68619 | 9/2001 |
| WO | WO02/06213 | 1/2002 |
| WO | WO02/018319 | 3/2002 |
| WO | WO02/069960 | 9/2002 |
| WO | WO02/076496 | 10/2002 |
| WO | WO03/062189 | 7/2003 |
| WO | WO03/062191 | 7/2003 |

OTHER PUBLICATIONS

Sebolt-Leopold, J., "Blockade Of The MAP Kinase Pathway Suppresses Growth Of Colon Tumors In Vivo," *Nature Medicine*, 1999, 5:7, 810-816.

* cited by examiner

*Primary Examiner*—Shailendra Kumar
(74) *Attorney, Agent, or Firm*—Bryan C. Zielinski; Galina M. Yakovleva

(57) ABSTRACT

This invention provides a novel polymorphic form of N-[(R)-2,3-dihydroxy-propoxy]-3,4-difluoro-2-(2-fluoro-4-iodo-phenylamino)-benzamide, as well a pharmaceutical compositions and therapeutic methods utilizing the polymorphic form.

19 Claims, 1 Drawing Sheet

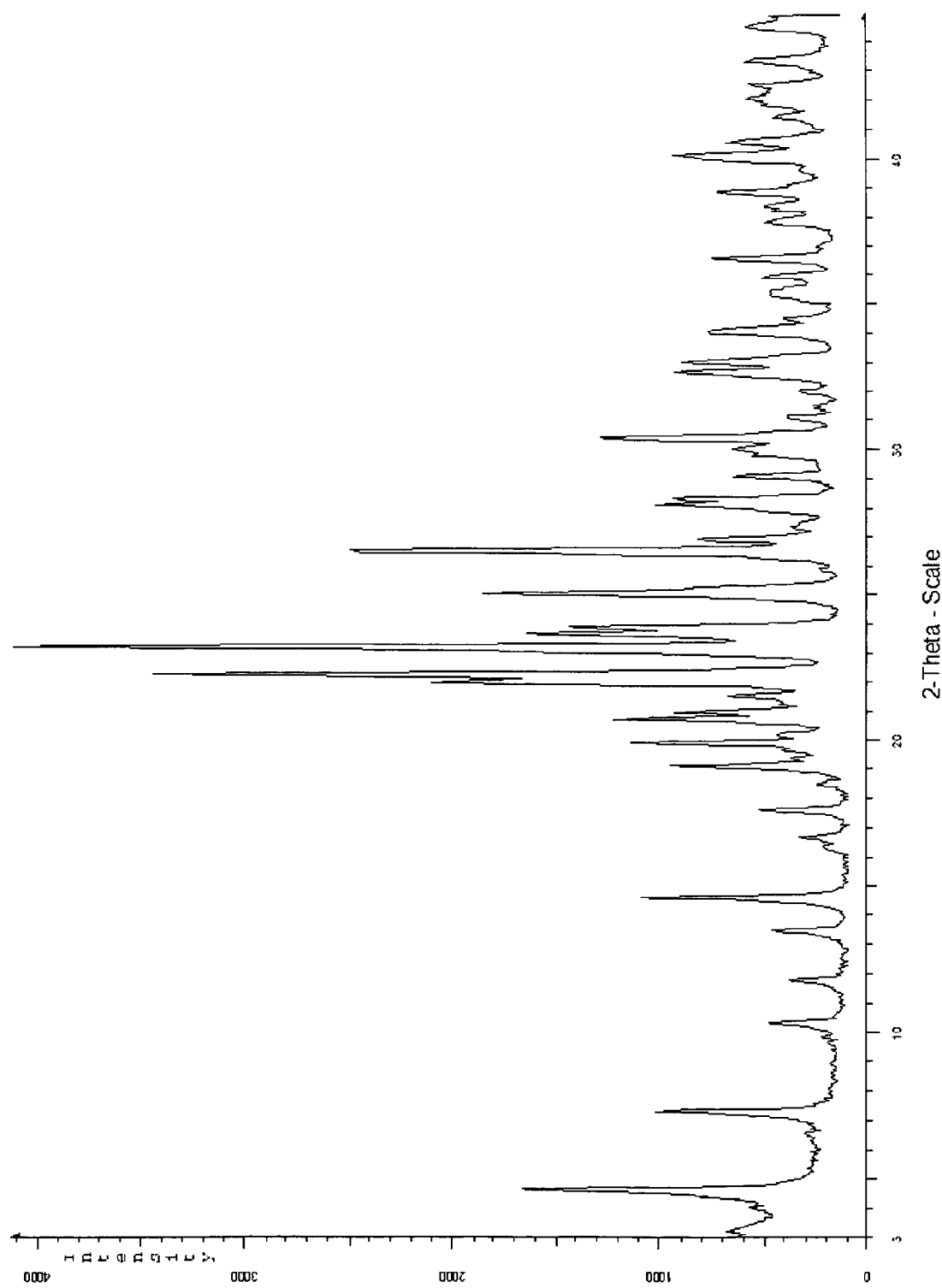

POLYMORPHIC FORM OF N-[(R)-2,3-DIHYDROXY-PROPOXY]-3,4-DIFLUORO-2-(2-FLUORO-4-IODOPHENYLAMINO)-BENZAMIDE

The present application claims benefit of U.S. Provisional Application Ser. No. 60/512,980, filed on Oct. 21, 2003, the entire disclosure of which is incorporated herein by reference.

FIELD OF THE INVENTION

This invention provides a novel polymorphic form IV of N-[(R)-2,3-dihydroxy-propoxy]-3,4-difluoro-2-(2-fluoro-4-iodo-phenylamino)-benzamide, as well as methods of preparing the polymorphic form, as well as pharmaceutical compositions and methods of treatment utilizing the polymorphic form.

BACKGROUND OF THE INVENTION

N-(2,3-Dihydroxypropoxy)-3,4-difluoro-2-[(2-fluoro-4-iodophenyl)amino]-benzamide is a MEK inhibitor described in WO 2002006213 A2 (Barrett et al.) and EP 1262176 A1 (Baragi et al.), the entire disclosure of which are incorporated herein by reference. MEK inhibitors are compounds which inhibit one or more of the family of mammalian enzymes known as MAP kinase kinases, which phosphorylate the MAP kinase subfamily of enzymes (mitogen-associated protein kinase enzymes) referred to as MAP kinases or ERKs (extracellular signal-regulating enzymes such as ERK1 and ERK 2). These enzymes regulate phosphorylation of other enzymes and proteins within the mammalian body. MEK 1 and MEK 2, as well as ERK1 and ERK 2, are dual specificity kinases that are present in all cell types and play a critical role in the regulation of cell proliferation and differentiation in response to mitogens and a wide variety of growth factors and cytokines. Upon activation, these enzymes control a cascade that can phosphorylate a large number of substrates, including transcription factors, the EGF receptor, phospholipase A2, tyrosine hydroxylase, and cytoskeletal proteins. One selective MEK inhibitor has been shown to be useful to treat a number of proliferative disorders, including psoriasis, restenosis, and cancer, as described in U.S. Pat. No. 5,525,625, incorporated herein by reference. A whole series of MEK inhibitors have been described as useful to prevent and treat septic shock, see WO 98/37881, incorporated herein by reference.

Crystalline polymorphs are different crystalline forms of the same compound. The term polymorph may or may not include other solid state molecular forms including hydrates (e.g., bound water present in the crystalline structure) and solvates (e.g., bound solvents other than water) of the same compound. Different crystalline polymorphs have different crystal structures due to a different packing of the molecules in the lattice. This results in a different crystal symmetry and/or unit cell parameters which directly influences its physical properties such the X-ray diffraction characteristics of crystals or powders. A different polymorph, for example, will in general diffract at a different set of angles and will give different values for the intensities. Therefore X-ray powder diffraction can be used to identify different polymorphs, or a solid form that comprises more than one polymorph, in a reproducible and reliable way (S. Byrn et al, Pharmaceutical Solids: A Strategic Approach to Regulatory Considerations, Pharmaceutical research, Vol. 12, No. 7, p. 945–954, 1995; J. K. Haleblian and W. McCrone, Pharmaceutical Applications of Polymorphism, Journal of Pharmaceutical Sciences, Vol. 58, No. 8, p. 911–929,1969).

Crystalline polymorphic forms are of interest to the pharmaceutical industry and especially to those involved in the development of suitable dosage forms. If the polymorphic form is not held constant during clinical or stability studies, the exact dosage form used or studied may not be comparable from one lot to another. It is also desirable to have processes for producing a compound with the selected polymorphic form in high purity when the compound is used in clinical studies or commercial products since impurities present may produce undesired toxicological effects. Certain polymorphic forms may exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies.

US 2004/0054172, the entire disclosure of which is incorporated herein by reference, provides crystalline Form I and Form II of N-[(R)-2,3-dihydroxy-propoxy]-3,4-difluoro-2-(2-fluoro-4-iodo-phenylamino)-benzamide (referred to as "Form I" and "Form II", respectively) or hydrates thereof, crystalline Form I and Form II of N-(2,3-dihydroxy-propoxy)-3,4-difluoro-2-(2-fluoro-4-iodo-phenylamino)-benzamide or hydrates thereof, and crystalline Form I and Form II of N-[(S)-2,3-dihydroxy-propoxy]-3,4-difluoro-2-(2-fluoro-4-iodo-phenylamino)-benzamide or hydrates thereof, which are useful as pharmaceutical agents, methods for their production and isolation, pharmaceutical compositions which include these compounds and a pharmaceutically acceptable carrier, and pharmaceutical methods of treatment. The disclosed crystalline compounds of US 2004/0054172 are useful as inhibitors of MEK.

SUMMARY OF THE INVENTION

In one embodiment, the present invention provides a crystalline form of N-[(R)-2,3-dihydroxy-propoxy]-3,4-difluoro-2-(2-fluoro-4-iodo-phenylamino)-benzamide, wherein the crystalline form is a substantially pure polymorph of Form IV.

In another embodiment, the invention provides a crystalline form of N-[(R)-2,3-dihydroxy-propoxy]-3,4-difluoro-2-(2-fluoro-4-iodo-phenylamino)-benzamide, wherein the crystalline form has a powder X-ray diffraction pattern comprising peaks at diffraction angles (2θ) of 4.6, 7.2, 14.6, 19.9, 23.2 and 26.5.

In another embodiment, the invention provides a crystalline form of N-[(R)-2,3-dihydroxy-propoxy]-3,4-difluoro-2-(2-fluoro-4-iodo-phenylamino)-benzamide, wherein the crystalline form has a powder X-ray diffraction pattern comprising peaks at diffraction angles (2θ) essentially the same as shown in FIG. 1.

In another embodiment, the invention provides a crystalline form of N-[(R)-2,3-dihydroxy-propoxy]-3,4-difluoro-2-(2-fluoro-4-iodo-phenylamino)-benzamide, wherein the crystalline form has a powder X-ray diffraction pattern comprising peaks at diffraction angles at approximately 4.6, 7.2, 14.6, 19.1, 19.9, 20.7, 22.0, 22.2, 23.2, 23.6, 23.9, 25.0, 26.5, 28.1, 28.3, 30.0, 30.4, 32.7, 33.0, 34.1, 36.6, 40.1, 42.1, 43.4 and 44.6.

In another embodiment, the invention provides a solid form of N-[(R)-2,3-dihydroxy-propoxy]-3,4-difluoro-2-(2- fluoro-4-iodo-phenylamino)-benzamide, wherein the solid form comprises Form IV and at least one of polymorphs of Forms I and II.

In another embodiment, the invention provides a process for making a polymorph Form IV of N-[(R)-2,3-dihydroxy-propoxy]-3,4-difluoro-2-(2-fluoro-4-iodo-phenylamino)-benzamide, the process comprising the steps of:

a) providing an amount of N-[(R)-2,3-dihydroxy-propoxy]-3,4-difluoro-2-(2-fluoro-4-iodo-phenylamino)-benzamide into a volume of a $C_1$–$C_4$ lower alkanol and water, the amount of the $C_1$–$C_4$ lower alkanol to water being at a ratio of from about 1:7 to about 1:13, at a temperature of from about 30° C. to about 40° C., to create a mixture of N-[(R)-2,3-dihydroxy-propoxy]-3,4-difluoro-2-(2-fluoro-4-iodo-phenylamino)-benzamide in the $C_1$–$C_4$ lower alkanol and water;

b) cooling the mixture of N-[(R)-2,3-dihydroxy-propoxy]-3,4-difluoro-2-(2-fluoro-4-iodo-phenylamino)-benzamide in the $C_1$–$C_4$ lower alkanol and water to a temperature from about 20° C. to less than about 30° C.; and c) separating the polymorph Form IV of N-[(R)-2,3-dihydroxy-propoxy]-3,4-difluoro-2-(2-fluoro-4-iodo-phenylamino)-benzamide from the $C_1$–$C_4$ lower alkanol and water.

In another embodiment, the invention provides a process for making a polymorph Form IV of N-[(R)-2,3-dihydroxy-propoxy]-3,4-difluoro-2-(2-fluoro-4-iodo-phenylamino)-benzamide, the process comprising the steps of:

a) providing an amount of N-[(R)-2,3-dihydroxy-propoxy]-3,4-difluoro-2-(2-fluoro-4-iodo-phenylamino)-benzamide into a volume of a $C_1$–$C_4$ lower alkanol and water, the amount of the $C_1$–$C_4$ lower alkanol to water being at a ratio of from about 1:7 to about 1:13, at a temperature of from about 30° C. to about 40° C., to create a mixture of N-[(R)-2,3-dihydroxy-propoxy]-3,4-difluoro-2-(2-fluoro-4-iodo-phenylamino)-benzamide in the $C_1$–$C_4$ lower alkanol and water;

b) cooling the mixture of N-[(R)-2,3-dihydroxy-propoxy]-3,4-difluoro-2-(2-fluoro-4-iodo-phenylamino)-benzamide in the $C_1$–$C_4$ lower alkanol and water to a temperature from about 20° C. to less than about 30° C.; and c) separating the polymorph Form IV of N-[(R)-2,3-dihydroxy-propoxy]-3,4-difluoro-2-(2-fluoro-4-iodo-phenylamino)-benzamide from the $C_1$–$C_4$ lower alkanol and water;

wherein the $C_1$–$C_4$ lower alkanol is ethanol.

In another embodiment, the invention provides a pharmaceutical composition comprising a crystalline form of N-[(R)-2,3-dihydroxy-propoxy]-3,4-difluoro-2-(2-fluoro-4-iodo-phenylamino)-benzamide, wherein the crystalline form is a substantially pure polymorph of Form IV.

In another embodiment, the invention provides a dosage form comprising a pharmaceutically effective amount of a crystalline form of N-[(R)-2,3-dihydroxy-propoxy]-3,4-difluoro-2-(2-fluoro-4-iodo-phenylamino)-benzamide, wherein the crystalline form is a substantially pure polymorph of Form IV and a pharmaceutically acceptable carrier.

In another embodiment, the invention provides a method of treating a mammalian disease condition mediated by MEK activity, the method comprising administering to a mammal in need thereof a therapeutically effective amount of a pharmaceutical composition comprising a crystalline form of N-[(R)-2,3-dihydroxy-propoxy]-3,4-difluoro-2-(2-fluoro-4-iodo-phenylamino)-benzamide, wherein the crystalline form is a substantially pure polymorph of Form IV.

In another embodiment, the invention provides a method of treating cancer in a mammal, the method comprising administering to the mammal a therapeutically effective amount of a pharmaceutical composition comprising a crystalline form of N-[(R)-2,3-dihydroxy-propoxy]-3,4-difluoro-2-(2-fluoro-4-iodo-phenylamino)-benzamide, wherein the crystalline form is a substantially pure polymorph of Form IV.

Definitions

The term "active agent" or "active ingredient" refers to a polymorphic form of N-[(R)-2,3-dihydroxy-propoxy]-3,4-difluoro-2-(2-fluoro-4-iodo-phenylamino)-benzamide or to a solid form that comprises two or more polymorphic forms of N-[(R)-2,3-dihydroxy-propoxy]-3,4-difluoro-2-(2-fluoro-4-iodo-phenylamino)-benzamide.

The term "$C_1$–$C_4$ lower alkanol" refers to $C_1$–$C_4$ lower alkanols which include methanol, ethanol, propanol, isopropanol, etc., with ethanol being a preferred alkanol.

The term "ambient temperature" refers to a temperature condition typically encountered in a laboratory setting. This includes the approximate temperature range of about 20 to about 30° C.

The term "aqueous base" refers to any organic or inorganic base. Aqueous bases include, by way of example only, metal bicarbonates, such as sodium bicarbonate, potassium carbonate, cesium carbonate, and the like.

The term "aromatic solvent" refers to an organic solvent possessing an aromatic moiety, including by way of example only, benzene, toluene, xylene isomers or mixtures thereof, and the like.

The term "chemical stability" refers to a type of stability in which a particular compound maintains its chemical integrity, and includes, but is not limited to, thermal stability, light stability, and moisture stability.

The term "detectable amount" refers to an amount or amount per unit volume that can be detected using conventional techniques, such as X-ray powder diffraction, differential scanning calorimetry, HPLC, FT-IR, Raman spectroscopy, and the like.

The term "exposing to humidity" refers to the process of exposing a substance to water vapor in a humidor, humidity chamber, or any apparatus capable of controlling relative humidity. The term may also describe the process of exposing a substance to ambient humidity as during storage.

The term "inert solvent" refers to any solvent or liquid component of a slurry that does not chemically react with other components in a solution or slurry. Inert solvents include, by way of example only aprotic solvents such as aromatic solvents, ethyl acetate, acetone, methyl tert-butylether, dioxane, THF, and the like. Protic solvents include, by way of example only, methanol, ethanol, propanol isomers, butanol isomers and the like.

The term "minimal amount" refers to the least amount of solvent required to completely dissolve a substance at a given temperature.

The term "polymorph" refers to different crystalline forms of the same compound and includes, but is not limited to, other solid state molecular forms including hydrates (e.g., bound water present in the crystalline structure) and solvates (e.g., bound solvents other than water) of the same compound.

The term "peak intensities" refers to relative signal intensities within a given X-ray diffraction pattern. Factors which can affect the relative peak intensities are sample thickness and preferred orientation (i.e., the crystalline particles are not distributed randomly).

The term "peak positions" as used herein refers to X-ray reflection positions as measured and observed in X-ray powder diffraction experiments. Peak positions are directly related to the dimensions of the unit cell.

The term "pharmaceutically acceptable, carrier, diluent, or vehicle" refers to a material (or materials) that may be included with a particular pharmaceutical agent to form a pharmaceutical composition, and may be solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

The term "pharmaceutical composition" refers to a mixture of one or more of the compounds or polymorphs described herein, or physiologically/pharmaceutically acceptable salts or solvates thereof, with other chemical components, such as physiologically/pharmaceutically acceptable carriers and excipients. The purpose of a pharmaceutical composition is to facilitate administration of a compound to an organism.

The term "recrystallize" refers to the process of completely dissolving a solid in a first solvent with heating if necessary, and then inducing precipitation, usually by cooling the solution, or by adding a second solvent in which the solid is poorly soluble.

The term "relative humidity" refers to the ratio of the amount of water vapor in air at a given temperature to the maximum amount of water vapor that can be held at that temperature and pressure, expressed as a percentage.

The term "relative intensity" refers to an intensity value derived from a sample X-ray diffraction pattern. The complete ordinate range scale for a diffraction pattern is assigned a value of 100. A peak having intensity falling between about 50% to about 100% on this scale intensity is termed very strong (vs); a peak having intensity falling between about 50% to about 25% is termed strong (s). Additional weaker peaks are present in typical diffraction patterns and are also characteristic of a given polymorph.

The term "slurry" refers to a solid substance suspended in a liquid medium, typically water or an organic solvent.

The term "separating from" refers to a step in a synthesis in which the desired agent is isolated from other non-desired agents, including, but not limited to any of the following steps: filtering, washing with extra solvent or water, drying with heat and or under vacuum.

The term "substantially pure" with reference to a particular polymorphic form of N-[(R)-2,3-dihydroxy-propoxy]-3,4-difluoro-2-(2-fluoro-4-iodo-phenylamino)-benzamide means the polymorphic form includes less than 15%, preferably less than 10%, preferably less than 5%, preferably less than 3%, preferably less than 1% by weight of impurities, including other polymorphic forms. Such purity may be determined, for example, by X-ray powder diffraction.

The term "2 theta value" or "2θ" refers to the peak position based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ).

The term "under vacuum" refers to typical pressures obtainable by a laboratory oil or oil-free diaphragm vacuum pump.

The term "X-ray powder diffraction pattern" refers to the experimentally observed diffractogram or parameters derived therefrom. X-Ray powder diffraction patterns are characterized by peak position (abscissa) and peak intensities (ordinate).

The term "cancer" includes, but is not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

The term "chronic pain" for purposes of the present invention includes, but is not limited to, neuropathic pain, idiopathic pain, and pain associated with chronic alcoholism, vitamin deficiency, uremia, or hypothyroidism. Chronic pain is associated with numerous conditions including, but not limited to, inflammation, arthritis, and post-operative pain.

The term "mediated by MEK activity" refers to biological or molecular processes that are regulated, modulated, activated or inhibited by MEK activity. The present invention includes methods of modulating or inhibiting MEK activity, for example in mammalian tissue, by administering polymorphic Form IV. The activity of polymorphic form IV as a mediator of MEK activity may be measured by any of the methods available to those skilled in the art, including in vivo and/or in vitro assays.

As used herein, the term "neuropathic pain" is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, post-operative pain, arthritis pain, and nerve injury between the peripheral nervous system and the central nervous system.

The term "pharmaceutically effective amount" or "therapeutically effective amount" refers to that amount of the compound or polymorph being administered which will relieve to some extent one or more of the symptoms of the disorder being treated. In reference to the treatment of cancer, a therapeutically effective amount refers to that amount which has at least one of the following effects:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

The terms "treat", "treating" and "treatment" for purposes of the present invention refer to prophylaxis or prevention, inhibition, amelioration or elimination of a named condition once the condition has been established, as well as the inhibition or prevention of the physiological mechanisms that allow onset and progression of the condition to the point that symptoms or manifestations of the condition become discoverable. With regard particularly to cancer, these terms simply mean that the life expectancy of an individual affected with a cancer will be increased or that one or more of the symptoms of the disease will be reduced.

BRIEF DESCRIPTION OF THE DRAWING

FIG. 1 is a Powder X-ray Diffractogram of Form IV N-(2,3-dihydroxy-propoxy)-3,4-difluoro-2-(2-fluoro-4-iodo-phenylamino)-benzamide (Y-axis=0 to 4,000 cps)

DETAILED DESCRIPTION OF THE INVENTION

This invention comprises a novel crystalline polymorph Form IV of N-[(R)-2,3-dihydroxy-propoxy]-3,4-difluoro-2-(2-fluoro-4-iodo-phenylamino)-benzamide, having the formula:

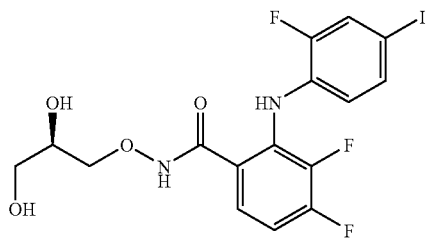

The polymorph Form IV of the invention is preferably substantially pure, meaning Form IV includes less than 15%, preferably less than 10%, preferably less than 5%, preferably less than 3%, preferably less than 1% by weight of impurities, including other polymorph forms of N-[(R)-2,3-dihydroxy-propoxy]-3,4-difluoro-2-(2-fluoro-4-iodo-phenylamino)-benzamide.

The solid forms of the present invention may also exist together in a mixture. For example, the mixture may include at least 5%, preferably at least 10%, preferably at least 50%, preferably at least 80% by weight of Form IV and at least one of polymorphs of Forms 1 and II. Mixtures of polymorphs form of the present invention will have X-ray diffraction peaks characteristic of each of the polymorphs forms present in the mixture. For example, a mixture of two polymorphs will have a powder X-ray diffraction pattern that is a convolution of the X-ray diffraction patterns corresponding to the substantially pure polymorphs.

Polymorph Form IV can be prepared by a process comprising the steps of:

a) entering an amount of N-[(R)-2,3-dihydroxy-propoxy]-3,4-difluoro-2-(2-fluoro-4-iodo-phenylamino)-benzamide into a volume of a $C_1$–$C_4$ lower alkanol and water, the amount of the $C_1$–$C_4$ lower alkanol to water being at a ratio of from about 1:7 to about 1:13, at a temperature of from above about 30° C. to about 40° C.;

b) stirring components of step a) to create a mixture of N-[(R)-2,3-dihydroxy-propoxy]-3,4-difluoro-2-(2-fluoro-4-iodo-phenylamino)-benzamide in the $C_1$–$C_4$ lower alkanol and water;

c) cooling the mixture of N-[(R)-2,3-dihydroxy-propoxy]-3,4-difluoro-2-(2-fluoro-4-iodo-phenylamino)-benzamide in the $C_1$–$C_4$ lower alkanol and water to a temperature from about 20° C. to less than about 30° C.;

d) separating the N-[(R)-2,3-dihydroxy-propoxy]-3,4-difluoro-2-(2-fluoro-4-iodo-phenylamino)-benzamide from the $C_1$–$C_4$ lower alkanol and water.

Within the process parameters discussed above are the steps of preparing polymorphic form IV by:

a) entering an amount of N-[(R)-2,3-dihydroxy-propoxy]-3,4-difluoro-2-(2-fluoro-4-iodo-phenylamino)-benzamide into a volume of a $C_1$–$C_4$ lower alkanol and water, the amount of the $C_1$–$C_4$ lower alkanol to water being at a ratio of from about 1:9 to about 1:11, at a temperature of from about 32° C. to about 38° C.;

b) stirring components of step a) to create a mixture of N-[(R)-2,3-dihydroxy-propoxy]-3,4-difluoro-2-(2-fluoro-4-iodo-phenylamino)-benzamide in the $C_1$–$C_4$ lower alkanol and water;

c) cooling the mixture of N-[(R)-2,3-dihydroxy-propoxy]-3,4-difluoro-2-(2-fluoro-4-iodo-phenylamino)-benzamide in the $C_1$–$C_4$ lower alkanol and water to a temperature from about 22° C. to about 28° C.;

d) separating the N-[(R)-2,3-dihydroxy-propoxy]-3,4-difluoro-2-(2-fluoro-4-iodo-phenylamino)-benzamide from the $C_1$–$C_4$ lower alkanol and water.

Within the processed described herein is a process in which from about 0.1 to about 5 kg of N-[(R)-2,3-dihydroxy-propoxy]-3,4-difluoro-2-(2-fluoro-4-iodo-phenylamino)-benzamide are mixed in a $C_1$–$C_4$ lower alkanol and water mixture having a volume of from about 7.5 to about 15 liters. Ethanol is a preferred $C_1$–$C_4$ lower alkanol.

X-ray diffraction patterns of the crystal form of the present invention were measured on a Rigaku Ultima+ diffractometer with CuK$_\alpha$ radiation.

Equipment

Rigaku Ultima+Diffractometer with an IBM-compatible interface equipped with 6 position autosampler, software=RigMeas v2.0 (Rigaku, December 1995) and JADE 3.1 (Materials Data, Inc.).

CuK$_\alpha$ radiation (40 mA, 40 kV, $\lambda$=1.5419 Å). Slits I and II at 0.5°, slit III at 0.3°.

Methodology Continuous $\theta/2\theta$ coupled scan: 3.00° to 45.00° in $2\theta$, scan rate of 0.2°/min: 15.0 sec/0.05° step.

Sample tapped out of vial and pressed onto zero-background silicon in aluminum holder. Sample width 5 mm.

Samples were stored and run at room temperature.

Samples were spun at 40 rpm around vertical axis during data collection.

Table 1 lists the X-ray powder diffraction pattern for crystalline Form IV of Compound A, expressed in terms of the 2-theta ("$2\theta$"), d-spacings or d(Å), and relative intensities by peak area with a relative intensity of >10% measured on a Rigaku Ultima+diffractometer with CuK$_\alpha$ radiation.

TABLE 1

| 2-Theta | d(Å) | Relative Intensity Area |
|---|---|---|
| 4.577 | 19.2922 | 34.8 |
| 7.245 | 12.1910 | 16.1 |
| 14.584 | 6.0686 | 23.0 |
| 19.091 | 4.6449 | 14.5 |
| 19.894 | 4.4592 | 14.1 |
| 20.697 | 4.2881 | 16.4 |
| 21.964 | 4.0434 | 43.3 |
| 22.245 | 3.9931 | 76.5 |
| 23.157 | 3.8378 | 100.0 |
| 23.648 | 3.7592 | 52.9 |
| 23.884 | 3.7226 | 33.2 |

TABLE 1-continued

| 2-Theta | d(Å) | Relative Intensity Area |
|---|---|---|
| 25.006 | 3.5580 | 54.7 |
| 26.491 | 3.3619 | 57.8 |
| 26.905 | 3.3110 | 12.8 |
| 28.103 | 3.1726 | 23.4 |
| 28.296 | 3.1514 | 17.2 |
| 29.962 | 2.9798 | 13.8 |
| 30.393 | 2.9385 | 29.9 |
| 32.653 | 2.7402 | 23.1 |
| 33.008 | 2.7115 | 25.2 |
| 34.054 | 2.6305 | 20.6 |
| 36.593 | 2.4536 | 12.6 |
| 40.093 | 2.2471 | 13.8 |
| 42.098 | 2.1446 | 20.5 |
| 43.360 | 2.0851 | 11.3 |
| 44.554 | 2.0320 | 14.7 |

Additionally, the invention provides a method of treating a proliferative disease in a patient in need thereof comprising administering a pharmaceutically or therapeutically effective amount of this polymorphic form IV of N-[(R)-2,3-dihydroxy-propoxy]-3,4-difluoro-2-(2-fluoro-4-iodo-phenylamino)-benzamide.

The invention also provides the use of a pharmaceutically or therapeutically effective amount of this novel polymorphic form IV of N-[(R)-2,3-dihydroxy-propoxy]-3,4-difluoro-2-(2-fluoro-4-iodo-phenylamino)-benzamide for the manufacture of a medicament for the treatment of a proliferative disease.

Furthermore, the invention provides methods of treating cancer, restenosis, psoriasis, autoimmune disease, atherosclerosis, osteoarthritis, rheumatoid arthritis, heart failure, chronic pain, and neuropathic pain in a patient in need thereof comprising administering a therapeutically effective amount of polymorphic form IV of N-[(R)-2,3-dihydroxy-propoxy]-3,4-difluoro-2-(2-fluoro-4-iodo-phenylamino)-benzamide.

Melanomas which may be treated with the methods herein include superficial spreading melanoma, also known as the Clark melanocytic nevus, nodular melanoma, lentigo maligna melanoma (also sometimes called Hutchinson's melanotic freckle), acral lentiginous melanoma, ocular melanomas, including conjunctiva melanoma and uveal (choroidal) melanoma, and less common melanomas, such as malignant melanomas of the oral and genital regions, such as vulval melanoma, and mucosal melanomas, including anorectal melanomas.

The invention also provides the use of a pharmaceutically or therapeutically effective amount of this novel polymorphic form IV of N-[(R)-2,3-dihydroxy-propoxy]-3,4-difluoro-2-(2-fluoro-4-iodo-phenylamino)-benzamide for the manufacture of a medicament for the treatment of cancer, restenosis, psoriasis, autoimmune disease, atherosclerosis, osteoarthritis, rheumatoid arthritis, heart failure, chronic pain, and neuropathic pain.

In addition, the invention provides a method for treating cancer in a patient in need thereof comprising administering a therapeutically effective amount of the polymorphic form described herein in combination with radiation therapy or at least one chemotherapeutic agent.

The disclosed compositions are useful as both prophylactic and therapeutic treatments for diseases or conditions related to the hyperactivity of MEK, as well as diseases or conditions modulated by the MEK cascade. Examples include, but are not limited to, stroke, septic shock, heart failure, osteoarthritis, rheumatoid arthritis, organ transplant rejection, and a variety of tumors such as ovarian, lung, pancreatic, brain, prostatic, and colorectal.

The invention further relates to a method for treating proliferative diseases, such as cancer, restenosis, psoriasis, autoimmune disease, and atherosclerosis. Other aspects of the invention include methods for treating MEK-related (including ras-related) cancers, whether solid or hematopoietic. Examples of cancers include brain, breast, lung, such as non-small cell lung, ovarian, pancreatic, prostate, renal, colorectal, cervical, acute leukemia, and gastric cancer. Further aspects of the invention include methods for treating or reducing the symptoms of xenograft (cell(s), skin, limb, organ or bone marrow transplant) rejection, osteoarthritis, rheumatoid arthritis, cystic fibrosis, complications of diabetes (including diabetic retinopathy and diabetic nephropathy), hepatomegaly, cardiomegaly, stroke (such as acute focal ischemic stroke and global cerebral ischemia), heart failure, septic shock, asthma, Alzheimer's disease, and chronic or neuropathic pain. Compounds of the invention are also useful as antiviral agents for treating viral infections such as HIV, hepatitis (B) virus (HBV), human papilloma virus (HPV), cytomegalovirus (CMV), and Epstein-Barr virus (EBV). These methods include the step of administering to a patient in need of such treatment, or suffering from such a disease or condition, a therapeutically effective amount of a disclosed compound, including crystal forms, or pharmaceutical composition thereof.

The invention also features methods of combination therapy, such as a method for treating cancer, wherein the method further includes providing to a recipient a pharmaceutically effective amount of polymorphic form IV of N-[(R)-2,3-dihydroxy-propoxy]-3,4-difluoro-2-(2-fluoro-4-iodo-phenylamino)-benzamide in combination with radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4(1H,3H)-pyrimidinedione (5FU), flutamide, and gemcitabine.

The chemotherapy or radiation therapy may be administered before, concurrently, or after the administration of a disclosed compound according to the needs of the patient.

Those skilled in the art will be able to determine, according to known methods, the appropriate therapeutically-effective amount or dosage of a compound of the present invention to administer to a patient, taking into account factors such as age, weight, general health, the compound administered, the route of administration, the type of pain or condition requiring treatment, and the presence of other medications. In general, an effective amount or a therapeutically-effective amount of this polymorphic form IV of N-[(R)-2,3-dihydroxy-propoxy]-3,4-difluoro-2-(2-fluoro-4-iodo-phenylamino)-benzamide will be between about 0.1 and about 1000 mg/kg per day, preferably between about 1 and about 300 mg/kg body weight, and daily dosages will be between about 1 and about 500 mg for an adult subject of normal weight, preferably between about 1 mg and 50 mg. As determined by a medical professional, a daily dose range for an adult human may be between about 1 mg and about 20 mg, in a single dosage or in divided doses. Commercially available capsules or other formulations (such as liquids and film-coated tablets) of, for example, 0.25 mg, 0.5 mg, 1 mg, 5 mg, 10 mg, 25 mg, 50 mg, 100 mg, 200 mg, 300 mg, or 400 mg can be administered according to the disclosed methods.

Pharmaceutically useful formulations utilizing N-[(R)-2,3-dihydroxy-propoxy]-3,4-difluoro-2-(2-fluoro-4-iodo-phenylamino)-benzamide are preferably formulated prior to administration. Therefore, another aspect of the present invention is a pharmaceutical composition comprising a pharmaceutically effective amount of N-[(R)-2,3-dihydroxy-propoxy]-3,4-difluoro-2-(2-fluoro-4-iodo-phenylamino)-benzamide and a pharmaceutically acceptable carrier. In making the compositions of the present invention, the active ingredient, N-[(R)-2,3-dihydroxy-propoxy]-3,4-difluoro-2-(2-fluoro-4-iodo-phenylamino)-benzamide, will usually be mixed with a carrier, or diluted by a carrier or enclosed within a carrier. Dosage unit forms or pharmaceutical compositions include tablets, capsules, pills, powders, granules, aqueous and nonaqueous oral solutions and suspensions, and parenteral solutions packaged in containers adapted for subdivision into individual doses.

Dosage unit forms can be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption acccelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

Specific examples of oral formulations in hard gelatin capsules may include dosages, for example, from 0.1 mg to 50 mg per capsule. The compositions my include the active drug substance, N-[(R)-2,3-dihydroxy-propoxy]-3,4-difluoro-2-(2-fluoro-4-iodo-phenylamino)-benzamide form IV, a diluent, such as microcrystalline cellulose, and a disintegrant, such as croscarmellose sodium. The composition may also contain a lubricant, such as stearic acid or magnesium stearate.

Examples of these oral formulations in hard gelatin capsules include those in which the active drug substance comprises from about 0.1–20% of the formulation, by weight, a diluent comprises from about 75–95%, a disintegrant comprises from about 3–7% and, optionally, a lubricant comprises from about 0.1–2%.

A 0.25 mg capsule may contain from about 0.15 to about 0.25% N-[(R)-2,3-dihydroxy-propoxy]-3,4-difluoro-2-(2-fluoro-4-iodo-phenylamino)-benzamide form IV, by weight, from about 93–95% microcrystalline cellulose, from about 4–6% croscarmellose sodium and, optionally, from about 0.5–1.5% magnesium stearate.

A 1 mg capsule may contain from about 0.7 to about 0.85% N-[(R)-2,3-dihydroxy-propoxy]-3,4-difluoro-2-(2-fluoro-4-iodo-phenylamino)-benzamide form IV, by weight, from about 92.5–95% microcrystalline cellulose, from about 4–6% croscarmellose sodium and, optionally, from about 0.5–1.5% magnesium stearate.

A 5 mg capsule may contain from about 4% to about 6% N-[(R)-2,3-dihydroxy-propoxy]-3,4-difluoro-2-(2-fluoro-4-iodo-phenylamino)-benzamide form IV, by weight, from about 87–93% microcrystalline cellulose, from about 4–6% croscarmellose sodium and, optionally, from about 0.5–1.5% magnesium stearate.

A 25 mg capsule may contain from about 14% to about 17% N-[(R)-2,3-dihydroxy-propoxy]-3,4-difluoro-2-(2-fluoro-4-iodo-phenylamino)-benzamide form IV, by weight, from about 76–83% microcrystalline cellulose, from about 4–6% croscarmellose sodium and, optionally, from about 0.5–1.5% magnesium stearate.

Hard gelatin capsule oral formulation of the type just described may be prepared by methods known in the art. An example includes blending and milling the active drug agent with the desired amount of disintegrant, such as croscarmellose sodium, and half the desired amount of diluent, such as microcrystalline cellulose. The second half of the diluent may then be milled and blended with the first mixture of active agent, diluent and disintegrant and the resulting composition blended. An optional lubricant, such as magnesium stearate, may then be added with additional blending. The total composition may then be measured and placed in hard gelatin capsules. Alternatively, the dry composition may be pressed into slugs using a tablet press, followed by additional milling of the resulting slugs. This final mixture may then be divided into the appropriate dosages and sealed in hard gelatin capsules.

It will be understood that N-[(R)-2,3-dihydroxy-propoxy]-3,4-difluoro-2-(2-fluoro-4-iodo-phenylamino)-benzamide can be readily prepared by methods known in the art. For instance, it may be prepared as described in the methods of WO 2002006213 A2 (Barrett et al.) beginning with the reaction of 2-fluoro-4-iodo-phenylamine (Registry No. 367-25-9) and 2,3,4-trifluoro-benzoic acid (Registry No. 61079-72-9) in the presence of an organic base, such as lithium diisopropylamide, to form 3,4-difluoro-2-(2-fluoro-4-iodo-phenylamino)-benzoic acid, which can then be reacted with (R)-O-(2,2-dimethyl-[1,3]dioxolan-4-ylmethyl)-hydroxylamine. The resulting product can be hydrolysed with aqueous acid to provide N-[(R)-2,3-Dihydroxy-propoxy]-3,4-difluoro-2-(2-fluoro-4-iodo-phenylamino)-benzamide.

EXAMPLES

Example 1

N-[(R)-2,3-Dihydroxy-propoxy]-3,4-difluoro-2-(2-fluoro-4-iodo-phenylamino)-benzamide (Form I)

Step A: To a solution of 3,4-difluoro-2-(2-fluoro-4-iodo-phenylamino)-benzoic acid (39.3 g, 100.0 mmol) in dry tetrahydrofuran (500 mL, 0.2 M), under nitrogen atmosphere, was added (R)-O-(2,2-dimethyl-[1,3]dioxolan-4-ylmethyl)-hydroxylamine (14.7 g, 100.0 mmol), followed by N-methylmorpholine (27.5 mL, 0.25 mole). The orange-colored solution was cooled with an ice-water bath. Diphenylphosphinic chloride (22.9 mL, 0.12 mole) was added dropwise. Some solid formed. The mixture was warmed to ambient temperature and stirred for 18 hrs. Water was added to quench the reaction and the tetrahydrofuran was evaporated in vacuo. The remaining oil was dissolved in ethyl acetate (500 mL), washed with a mixture of saturated brine and saturated sodium bicarbonate (1:1) two times. The ethyl acetate was removed and the crude oily solid was purified by flash chromatography (silica gel, hexane-acetone/2:1) to give N-((R)-2,2-dimethyl-[1,3]dioxolan-4-ylmethoxy)-3,4-difluoro-2-(2-fluoro-4-iodo-phenylamino)-benzamide as an off-white solid after drying in a vacuum oven at 40° C. for 20 hrs: 41.7 g (79.8%), m.p. 124–125° C. The impure fractions were combined and purified by a second column chromatography using the same condition to give a $2^{nd}$ batch of 6.4 g (12.3%), mp 124–125° C., total yield 48.1 g (92.1%). $^1$H NMR ($d^6$-DMSO): δ 11.9 (s, br, 1H), 8.7 (s, br, 1H), 7.6 (d, 1H, J=10.99 Hz), 7.4 (m, 2H), 7.2 (m, 1H), 6.7 (m, 1H), 4.2 (m, 1H), 4.0 (t, 1H, J1=8.3 Hz, J2=6.8 Hz), 3.8 (m, 2H), 3.7 (m, 1H), 1.3 (s, 3H), 1.2 (s, 3H); $^{19}$F NMR ($d^6$-DMSO): δ–128.0, –133.1, –144.3; MS: 523 ($M^+$+1).

Step B: N-((R)-2,2-Dimethyl-[1,3]dioxolan-4-ylmethoxy)-3,4-difluoro-2-(2-fluoro-4-iodo-phenylamino)-benzamide (22.3 g, 42.7 mmol) was suspended in methanol (223 mL, 10 mL/g), and a solution of pTsOH.$H_2$O (4.1 g, 21.35 mmol) in water (22.3 mL) was added. The mixture was stirred at ambient temperature for 18 hrs, during which all solids dissolved to give a colorless, clear solution. The solution was concentrated and extracted with ethyl acetate (2×300 mL). The organic solution was washed with sodium bicarbonate, dried over MgSO$_4$. After filtration, the filtrate was concentrated, and co-evaporated with heptane to give a foaming solid. To this solid was added hexane-CH$_2$Cl$_2$ (1:1, 100 mL) and the mixture was stirred for 30 min. A white solid formed, which was filtered, washed with hexane. The solid was recrystallized from hexane-AcOEt to give N-((R)-2,3-dihydroxy-propoxy)-3,4-difluoro-2-(2-fluoro-4-iodo-phenylamino)-benzamide as white crystals, 13.57 g (65.9%), after drying at 60° C. vacuum oven for 3 days. A second crop of 5.05 g was obtained from the mother liquor, after recrystallization from the same solvent system. The total yield was 18.62 g (90.4%): m.p. 89–90° C. (Form II). The combined crystals were ground with a set of mortar and pestle to fine powder, and dried at 60° C. in a vacuum oven for 3 days: m.p. 117–118° C. (Form I); [α]=–2.05° (c=1.12, methanol); Analysis: Calcd. For: $C_{16}H_{14}F_3I_1N_2O_4$: C, 39.85; H, 2.93; N, 5.81; F, 11.82, I, 26.32. Found: C, 39.95; H, 2.76; N, 5.72; F, 11.71; I, 26.53. $^1$NMR (400 MHz, DMSO-$d_6$) δ 11.87 (s, 1H), 8.69 (s, 1H), 7.54 (dd, 1H, J=10.9, 1.5), 7.32–7.38 (m, 2H), 7.17 (dd, 1H, J=16.8, 9.0), 6.61–6.66 (cm, 1H), 4.82 (bs, 1H), 4.58 (bs, 1H), 3.84–3.85 (m, 1H), 3.71–3.64 (cm, 2H), 3.33 (2H, partially hidden by HDO).

Example 2

N-[(R)-2,3-Dihydroxy-propoxy]-3,4-difluoro-2-(2-fluoro-4-iodo-phenylamino)-benzamide (Form II)

Step A: To a solution of 3,4-difluoro-2-(2-fluoro-4-iodo-phenylamino)-benzoic acid (2.25 g, 5.10 mmol) in dry tetrahydrofuran under nitrogen atmosphere, at –15 C was added diphenylphosphinic chloride (1.26 mL, 6.63 mole) dropwise. After stirring 20 min., N-methyl morpholine (0.70 mL, 6.375 mmol) was added and the reaction stirred an additional 20 min. (R)-O-(2,2-dimethyl-[1,3]dioxolan-4-ylmethyl)-hydroxylamine (0.748 g, 5.1 mmol) was added and the reaction stirred for 1 hour, at which point N-methylmorpholine (0.7 mL, 6.37 mmol) was added. The mixture was warmed to ambient temperature and stirred for 12 h. The reaction was concentrated in vacuo and then diluted with EtOAc. The organic layer was washed with saturated NaHCO$_3$ (2×), brine (1×), dried over Na$_2$SO$_4$, filtered and concentrated. The crude product was purified on SiO2 using 4:1 hexane/EtOAc as elutant to provide 1.82 g (68%) of a brownish red solid.

Step B: N-((R)-2,2-Dimethyl-[1,3]dioxolan-4-ylmethoxy)-3,4-difluoro-2-(2-fluoro-4-iodo-phenylamino)-benzamide (0.210 g, 0.40 mmol) was suspended in 10:1 methanol/H$_2$O and pTsOH.H$_2$O (0.008 g, 0.04 mmol) was added. The mixture was stirred at ambient temperature for 18 hrs, during which all solids dissolved to give a colorless, clear solution. The solution was diluted with EtOAc. The organic solution was washed with sodium bicarbonate (2×), brine (1×) and dried over Na$_2$SO$_4$. After filtration, the filtrate was concentrated, and recrystallized from EtOAc and heptane. This solid was washed with heptane-CH$_2$Cl$_2$ (1:1 and dried in vacuo at 60 C to give N-((R)-2,3-Dihydroxy-propoxy)-3,4-difluoro-2-(2-fluoro-4-iodo-phenylamino)-benzamide as a white solid, (0.136 g, 70%). Product shrinks at 90.8 C, melts at 115–117° C. Analysis shows C, 40.92; H, 3.16; N, 5.41, F, 11.30; I, 23.92 (6.75% EtOAc, 0.96% heptane).

Example 3

N-[(R)-2,3-Dihydroxy-propoxy]-3,4-difluoro-2-(2-fluoro-4-iodo-phenylamino)-benzamide (Form IV)

To a flask containing 3,4-difluoro-2-(2-fluoro-4-iodo-phenylamino)-benzoic acid (2.6 kg, 6.6 mol) and N,N'-carbonyldiimidazole (1.1 kg, 6.8 mol) under nitrogen atmosphere, was added 12 L of dry acetonitrile. After stirring at 22°±5° C. for about 90 minutes, a solution of (R)-O-(2,2-dimethyl-[1,3]dioxolan-4-ylmethyl)-hydroxylamine in toluene was added (8.5 L total volume, about 8 moles of amine). The solution was stirred for at least 6 hours at 22°±5 C. Aqueous hydrochloric acid (9 L, 1.5 molar) was added, and after stirring for about 5 minutes, the layers were separated. Aqueous hydrochloric acid (9 L, 1.5 molar) was added to the remaining top layer, and after stirring for about 20 hours, the layers were separated. The remaining top layer was concentrated by vacuum distillation, and then diluted with 15 L toluene and 2 L ethanol. The mixture was warmed to 35–45° C. and diluted with 20 L warm water, then cooled to 0–5° C. The product was collected by filtration and washed with 2 L toluene. The product was recrystallized by dissolving in 12 L toluene and 2 L ethanol (50°±5 C), adding 10 L water and cooling to 0–5° C. After collecting the product by filtration and washing with toluene, the product was dried in a vacuum oven resulting in 2.6 kg of N-[(R)-2,3-dihydroxypropoxy]-3,4-difluoro-2-(2-fluoro-4-iodo-phenylamino)-benzamide.

2.4 kg of the above compound as a mixture of different crystalline forms was stirred in a mixture of 10 L water and 1 L ethanol at 35±5° C. for 20–30 hours, then cooled to 25±5° C. The product was collected by filtration and washed with 1 L of water, then dried in a vacuum oven at 65° C. This resulted in 2.3 kg of material which was greater than 90% Form IV. Note: DSC analysis shows an onset of melting at 110° C. with only a small amount of the peak with an onset of melting at 117° C.

What is claimed is:

1. A crystalline form of N-[(R)-2,3-dihydroxy-propoxy]-3,4-difluoro-2-(2-fluoro-4-iodo-phenylamino)-benzamide, wherein the crystalline form is a substantially pure polymorph of Form IV.

2. The crystalline form of claim 1, wherein the crystalline form has a powder X-ray diffraction pattern comprising peaks at diffraction angles (2θ) of about 4.6, 7.2, 14.6, 19.9, 23.2 and 26.5.

3. The crystalline form of claim 1, wherein the crystalline form has a powder X-ray diffraction pattern comprising peaks at diffraction angles (2θ) essentially the same as shown in FIG. 1.

4. A solid form of N-[(R)-2,3-dihydroxy-propoxy]-3,4-difluoro-2-(2-fluoro-4-iodo-phenylamino)-benzamide, wherein the solid form comprises Form IV and at least one of polymorphs of Forms I and II.

5. A process for making a polymorph Form IV of N-[(R)-2,3-dihydroxy-propoxy]-3,4-difluoro-2-(2-fluoro-4-iodo-phenylamino)-benzamide, the process comprising the steps of:
   a) providing an amount of N-[(R)-2,3-dihydroxy-propoxy]-3,4-difluoro-2-(2-fluoro-4-iodo-phenylamino)-benzamide into a volume of a $C_1$–$C_4$ lower alkanol and water, the amount of the $C_1$–$C_4$ lower alkanol to water being at a ratio of from about 1:7 to about 1:13, at a temperature of from about 30° C. to about 40° C., to create a mixture of N-[(R)-2,3-dihydroxy-propoxy]-3,4-difluoro-2-(2-fluoro-4-iodo-phenylamino)-benzamide in the $C_1$–$C_4$ lower alkanol and water;
   b) cooling the mixture of N-[(R)-2,3-dihydroxy-propoxy]-3,4-difluoro-2-(2-fluoro-4-iodo-phenylamino)-benzamide in the $C_1$–$C_4$ lower alkanol and water to a temperature from about 20° C. to less than about 30° C.; and
   c) separating the polymorph Form IV of N-(R)-2,3-dihydroxy-propoxyl-3,4-difluoro-2-(2-fluoro-4-iodo-phenylamino)-benzamide from the $C_1$–$C_4$ lower alkanol and water.

6. The process of claim 5, wherein the $C_1$–$C_4$ lower alkanol is ethanol.

7. A pharmaceutical composition comprising the crystalline form of claim 1.

8. A dosage form comprising a pharmaceutically effective amount of the crystalline form of claim 1 and a pharmaceutically acceptable carrier.

9. A method of treating a mammalian disease condition mediated by MEK activity, the method comprising administering to a mammal in need thereof a therapeutically effective amount of the pharmaceutical composition of claim 7.

10. The dosage form of claim 8, wherein the amount of Form IV of N-[(R)-2,3-dihydroxy-propoxy]-3,4-difluoro-2-(2-fluoro-4-iodo-phenylamino)-benzamide, is from 0.1 to 50 mg.

11. The dosage form of claim 8, wherein the amount of Form IV of N-[(R)-2,3-dihydroxy-propoxy]-3,4-difluoro-2-(2-fluoro-4-iodo-phenylamino)-benzamide, is from 1 to 20 mg.

12. The dosage form of claim 8, wherein the dosage form is an oral dosage form.

13. The dosage form of claim 12, wherein the dosage form is a tablet or a capsule.

14. The dosage form of claim 13, wherein the capsule comprises from 0.1 to 20% of of Form IV of N-[(R)-2,3-dihydroxy-propoxy]-3,4-difluoro-2-(2-fluoro-4-iodo-phenylamino)-benzamide, from 75 to 95% of a diluent, and from 3 to 7% of a disintegrant.

15. The dosage form of claim 14, wherein the capsule further comprises from 0.1 to 2% of a lubricant.

16. The dosage form of claim 15, wherein the diluent is microcrystalline cellulose, the disintegrant is croscarmellose sodium, and the lubricant is stearic acid or magnesium stearate.

17. The process of claim 5, wherein N-[(R)-2,3-dihydroxy-propoxy]-3,4-difluoro-2-(2-fluoro-4-iodo-phenylamino)-benzamide is prepared by a method comprising:
   a) coupling o-{[(4R)-2,2-dimethyl-1,3-dioxolan-4-yl]methyl}hydroxylamine with 3,4-difluoro-2-(2-fluoro-4-iodophenylamino)-benzoic acid using 1,1-carbonyldiimidazole to form N-{[(4R)-2,2-dimethyl-1,3-dioxolan-4-yl]methoxy}-3,4-difluoro-2-[(2-fluoro-4-iodophenyl)amino]benzamide; and
   b) deprotecting N-{[(4R)-2,2-dimethyl-1,3-dioxolan-4-yl]methoxy}-3,4-difluoro-2-[(2-fluoro-4-iodophenyl)amino]benzamide to produce N-[(R)-2,3-dihydroxy-propoxy]-3,4-difluoro-2-(2-fluoro-4-iodo-phenylamino)-benzamide.

18. The process of claim 17, wherein the method for preparing N-[(R)-2,3-dihydroxy-propoxy]-3,4-difluoro-2-(2-fluoro-4-iodo-phenylamino)-benzamide, further comprises a step of recrystallizing of N-[(R)-2,3-dihydroxy-propoxy]-3,4-difluoro-2-(2-fluoro-4-iodo-phenylamino) benzamide.

19. The process of claim 18, wherein recrystallizing of N-[(R)-2,3-dihydroxy-propoxy]-3,4-difluoro-2-(2-fluoro-4-iodo-phenylamino)-benzamide, is carried out in a mixture of toluene, ethanol and water.

* * * * *